United States Patent [19]

Lyons

[11] Patent Number: 4,509,362
[45] Date of Patent: Apr. 9, 1985

[54] DEVICE FOR TESTING GAME BALLS

[76] Inventor: Robert V. Lyons, 516 LaForce, Zephyrhills, Fla. 33599

[21] Appl. No.: 514,106

[22] Filed: Jul. 15, 1983

[51] Int. Cl.³ ............................................. G01N 3/52
[52] U.S. Cl. .......................................... 73/79; 73/13
[58] Field of Search ................................ 73/79, 13, 12

[56] References Cited

U.S. PATENT DOCUMENTS

| | | | |
|---|---|---|---|
| 1,504,871 | 8/1924 | Covington | 73/79 |
| 3,859,841 | 1/1975 | Evans et al. | 73/79 X |
| 4,006,626 | 2/1977 | Ruzicka et al. | 73/79 X |

Primary Examiner—Donald J. Yusko
Assistant Examiner—E. Harding
Attorney, Agent, or Firm—Frijouf, Rust & Pyle

[57] ABSTRACT

A device is disclosed for testing the resilience of a game ball. The device comprises a tubular member having an opening at one end for receiving a game gall to be tested. A striking surface on the other end of the tubular member and calibrated markings along the length of the tubular member indicate the degree of resiliency of the game ball by virtue of the distance the game ball rebounds from the striking surface when the ball is dropped from the opening.

13 Claims, 7 Drawing Figures

DEVICE FOR TESTING GAME BALLS

BACKGROUND OF THE INVENTION

1. Field of the Invention

The invention relates to a device for testing the resiliency of balls such as golf balls, tennis balls, baseballs and the like.

2. Information Disclosure Statement

Over the years, serious golfers have recognized the distance traveled by a golf ball when driving off a tee will vary by considerable yardage dependent upon the resiliency of the golf ball. Heretofore it has been the practice of golfers to test a golf ball by dropping a golf ball onto a hard surface such as a concrete path or a golf cart path and observing the height to which the ball rebounds. However, not only is this procedure inaccurate in that the surface will vary in hardness, but also there is a danger that the golf ball will be damaged upon striking a rough surface. The resiliency of a golf ball can be lost for a number of reasons and it can be demonstrated experimentally that a loss of 5–10 percent in resiliency, which is not at all uncommon, can result in a loss of 10–20 yards off the tee. One of the reasons for the loss in resiliency is aging, whether or not the golf ball has been stored in the pocket of a golf bag or on the shelf of a sporting goods store. Another reason for this loss in resiliency is exposure to the sun or water. Sometimes a golf ball that has been lost in the rough is found by someone and sold as like new. Such a golf ball may well have lost much of its original resiliency. Cold weather also has a profound effect on the resiliency of the golf ball. The low temperature tends to embrittle the rubber structure of the golf ball. Various devices have been proposed to test the quality of golf balls, but these have proven cumbersome and not suitable as a portable testing device such as can be taken by a golfer right on to a golf course or that can be used during a golfing tournament.

U.S. Pat. No. 1,984,904 to Warshaw et al. relates to an impact testing machine in which two impact heads simultaneously apply blows to a golf ball to be tested and to a golf ball of known characteristics. U.S. Pat. No. 2,314,063 to Anderson et al. discloses an apparatus for testing golf balls as to their resiliency by means of complex electronic circuitry. U.S. Pat. No. 4,396,765 to Rathmell relates to an apparatus for testing the consistency and distance characteristics of golf balls. U.S. Pat. No. 4,006,626 to Ruzika discloses a golf ball tester in which the golf ball is guided by means of partial vacuum.

Various other devices have been proposed for testing the quality, shape, resiliency, weight and flight characteristics of baseballs, tennis balls, squash balls and the like, but the prior art of record has not filled the long felt need among sporting persons for a simple to use and inexpensive device which is portable and easy to manufacture. Tennis players have traditionally bounced a tennis ball on the tennis court surface before serving in order to test the resiliency of the ball but such a method of testing is to say, at the least, inaccurate, because it depends on several factors including the force with which the player throws the ball onto the court surface, the hardness of the court surface and the determination by the player of the force with which the tennis ball rebounds.

Although the aforementioned patents solve many of the needs of the prior art for testing the resiliency of game balls, these devices have all suffered from the problem that they have not been suitable for use, for example, by the golfer as part of his golfing equipment, or can be carried in his golf bag. Therefore, it is the primary object of this invention to provide a device that overcomes the aforementioned inadequacies of the prior art devices and provides an improvement which significantly contributes to the ease with which a player can test the resiliency of his game balls, particularly on the golf course.

Another object of this invention is to provide a simple and inexpensive device that will enable players to quickly test the condition of a game ball before the game.

Another object of this invention is to provide a device for testing the resiliency of game balls in which a tubular member has an opening for receiving a game ball to be tested. The game ball falls under the force of gravity and strikes an impact surface at the end of the tubular member and rebounds to a height dependent upon the resiliency of the game ball.

Another object of the invention is to provide a device for testing the resiliency of game balls comprising two parts, first a tubular member for guiding the game ball and secondly a steel insert secured within one end of the member remote from the end of said member where the game ball is inserted.

Another object of this invention is to provide a device for testing the resiliency of game balls wherein calibrated markings on a tubular member provide a visual indication of the degree of resiliency of said game ball by virtue of the distance said game ball rebounds upon striking the steel insert secured at one end of the tubular member.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the disclosure. Particularly with regard to the use of the invention disclosed herein, this should not be construed as limited to the testing of golf balls, but should include the testing of other balls such as tennis balls, squash balls, table tennis balls and the like.

SUMMARY OF THE INVENTION

The testing device of the present invention is defined by the appended claims with a specific embodiment shown in the attached drawings. For the purpose of summarizing the invention, the invention relates to a device for testing the resiliency of game balls or the like. The device comprises a tubular member having an opening at one end for receiving a game ball to be tested. An insert secured within the other end of the tubular member provides a striking surface to rebound the game ball to a calibrated marking on the tubular member. The distance the game ball rebounds is proportional to the degree of resiliency of the game ball.

In a more specific embodiment of the invention, the device is of a two-piece construction comprising a tubular member opening at one end and having graduated markings thereon with a cylindrical insert secured within the other end of the tubular member. In use of the device, the tubular member is held in a substantially vertical position and the game ball is inserted within the top opening and allowed to fall under the force of gravity to strike the insert at the bottom of the tubular member and to rebound a distance, dependent upon the resiliency of the game ball. The height to which the game ball rebounds is observed and corresponds with one of the calibrated markings along the length of the tubular member.

The foregoing has outlined rather broadly the more pertinent and important features of the present invention in order that the detailed description of the invention that follows may be better understood and so that the present contribution to the art can be more fully appreciated. Additionally, features of the invention will be described hereinafter which form the subject of the claims of the invention. It should be appreciated by those skilled in the art that the conception and specific embodiment disclosed may be readily utilized as a basis for modifying or designing other devices for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following description taken in conjunction with the accompanying drawings in which.

Similar reference characters refer to similar parts throughout the several views of the drawings.

DETAILED DESCRIPTION

Figure 1:
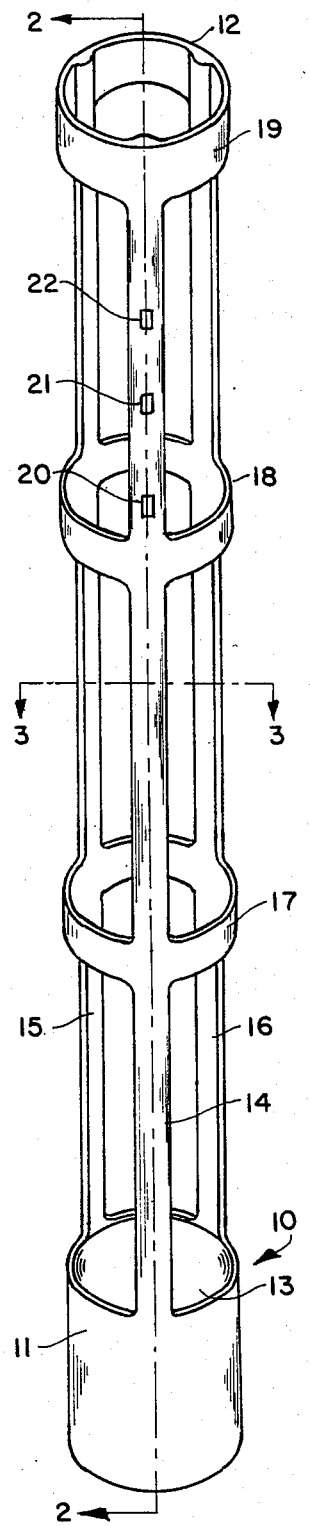
FIG. 1 is a perspective view of the testing device of the present invention.

FIG. 1 is a perspective view of a game ball testing device generally designated 10 comprising a tubular member 11 having at one end thereof an opening 12 for the insertion of a game ball to be tested. An insert is provided with a substantially planar striking surface 13 against which a game ball to be tested will rebound when dropped through opening 12 when tubular member 11 is held in a vertical position. Longitudinally extending guides 14, 15, and 16 serve the purpose of guiding the falling game ball toward the impact surface 13.

As illustrated with reference to FIGS. 2 and 3, the guides 14, 15, and 16 protrude inwardly relative to the tubular member so that a game ball will not come into contact with bands 17, 18 and 19, but will be guided by guides 14, 15, and 16. The longitudinal guides 14, 15, and 16 are substantially spaced equidistant one from the other so as to form a cage for the game ball to be tested. Calibrated markings 20, 21 and 22 are molded or printed on the external surface of each one of the longitudinal guides at a location between bands 18 and 19. The lower marking 20 can have an indication such as "dead ball" while the other marking 22 may have an indication such as "live ball". The intermediate marking can indicate an "old ball". In a preferred embodiment of the present invention, one of the guides such as 14 has therein three calibrated markings 20, 21 and 22, which markings have been calibrated for golf balls of 80 compressions. Another guide, such as 15, also has three calibrated markings as before, but calibrated for golf balls having 90 compressions. The guide 16 with its three calibrated markings is calibrated for game balls of the 100 compression type.

Figure 2:
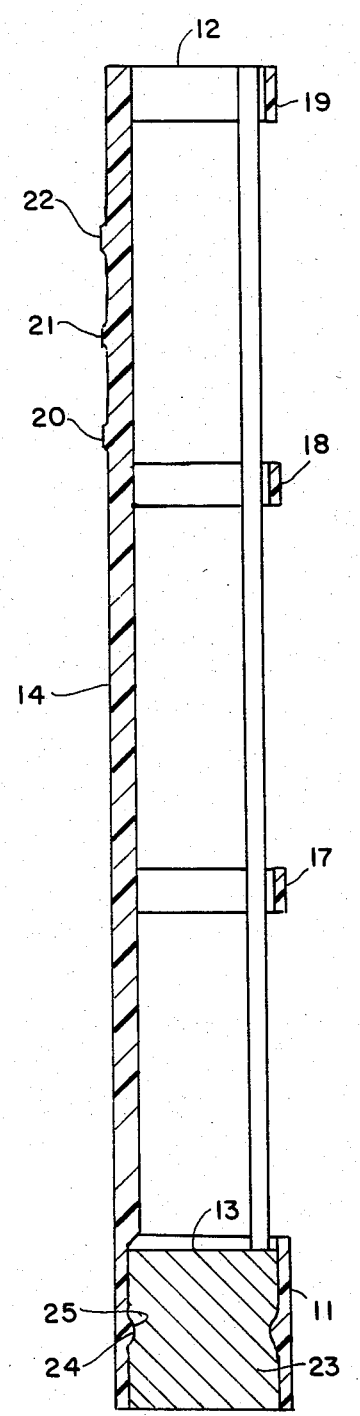
FIG. 2 is a sectional view of the game ball testing device taken on the line 2—2 of FIG. 1.

Referring to FIG. 2, the location of the insert 23 within the tubular member 11 is shown with the insert 23 having a planar striking surface 13 towards the opening 12. Inward projections 24 formed integrally with tubular member 11 cooperate with an annular groove 25 on the cylindrical insert 23 to fixedly secure the insert within the member 11.

Figure 3:
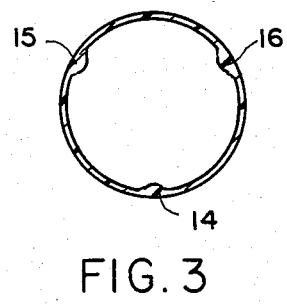
FIG. 3 is a sectional view taken along line 3—3 of FIG. 1.

FIG. 3 is a sectional view on line 3—3 of FIG. 1 in which longitudinally extending guides 14, 15 and 16 protrude inwardly along the entire length from opening 12 to striking surface 13 of insert 23.

Figure 4:
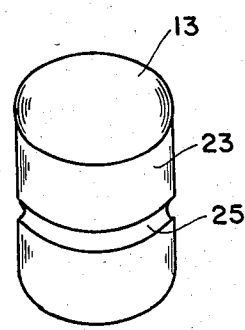
FIG. 4 is a perspective view of an insert incorporated in the testing device.

FIG. 4 shows in more detail the cylindrical insert 23 having an impact surface 13 and annular groove 25 for locating the insert within the tubular member.

Figure 5:
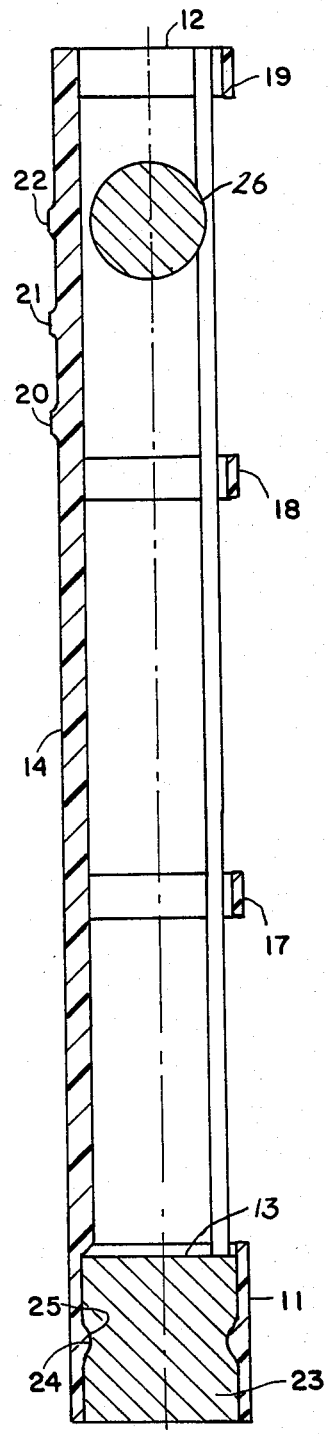
FIGS. 5–7 are views of the game ball testing device the same as that shown in FIG. 2 but showing different game balls rebounding to different heights.
Figure 6:
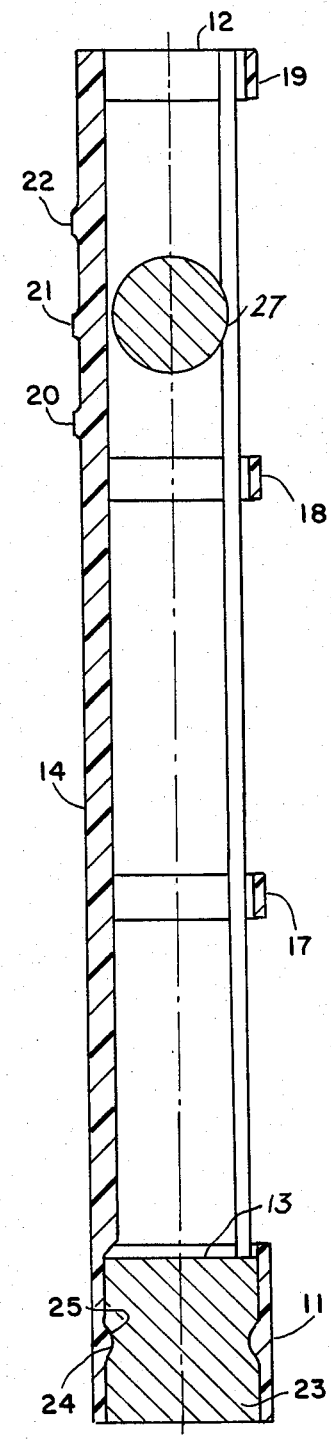
Figure 7:
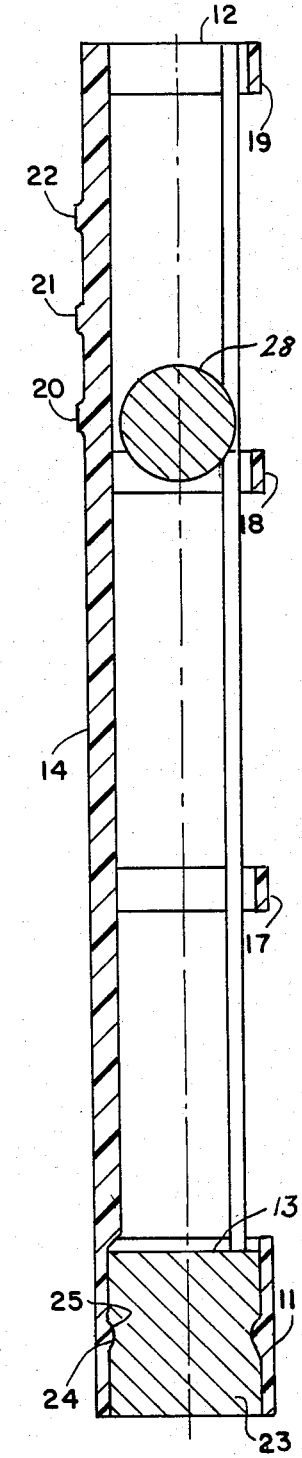

FIGS. 5–7 show different game balls rebounding from striking surfaces 13 to different heights. Referring to FIG. 5, the golf ball 26 is illustrated as having rebounded from striking surface 13 to a height corresponding with mark 22 thus indicating the ball as being in a live condition. FIG. 6 shows a golf ball 27 having rebounded to mark 21 indicating an old ball, while the golf ball 28 of FIG. 7 reaches a height equivalent to mark 20, indicating the ball is in a dead condition.

In use of the device, a golf ball to be tested is inserted into opening 12 with the tubular member being held in a vertical position. The ball drops under the force of gravity and is guided by guides 14, 15 and 16 towards the striking surface 13 of insert 23. The ball rebounds from surface 13 to a height dependent upon the resiliency and condition of the golf ball. If an 80 compression golf ball is being tested, the height to which the ball rebounds will be observed in relation to the calibrated markings on guide 14. If the ball is observed to rebound only to the height of marking 20, the ball is in a "dead" condition. If it rebounds to marking 21 or 22, the ball is observed to be "old" or in in a "live" condition, respectively. The tubular member 11 may be formed of any suitable plastic material; the insert may be of steel. A typical embodiment of the present invention may have the following dimensions: length of tubular member 11, 49 inches; internal diameter of tubular member 11, $1\frac{7}{8}$ inches; wall thickness of member 11, 0.06 to 0.09 inches; internal circle formed by guides 14, 15 and 16, $1\frac{3}{4}$ inches; width of band 19, 1 inch; width of band 18, $\frac{1}{2}$ inch; width of band 17, $\frac{1}{2}$ inch; length of guides 14, 15 and 16, 46 inches each; width of each guide, $\frac{3}{8}$ inches; distance from lower end of tubular member 11 to lower ends of band 17, $16\frac{1}{2}$ inches; and the distance from lower end of tubular member 11 to the lower edge of band 18, 28 inches. The external diameter of the steel insert 23 and $1\frac{7}{8}$ inches.

An important feature of the present invention is the simplicity with which the same can be manufactured because the tubular member is a one-piece molding of a plastic material having a simple metal insert at one end that can easily be secured within one end of the tubular molding. For example, the metal insert can be positioned in place during the molding process. The precut groove around the metal insert will be filled by plastic material which simultaneously forms the tubular member. This simplicity of manufacture is a distinct improvement over prior art proposals, all of which involved relatively complex manufacturing processes and the subsequent high cost of production.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A device for testing a game ball comprising in combination:
   a substantially tubular member having a top opening for receiving the game ball inserted therein when said tubular member is in a vertical position;
   said opening enabling the operator to drop the game ball from a predetermined position on said tubular member;
   said tubular member further including;
   a plurality of vertically spaced cylindrical bands;
   at least three vertically extending guides interconnecting said bands;
   said guides being equidistantly spaced about said cylindrical bands;
   a striking surface secured to said tubular member in proximity to a bottom portion of said tubular member when said tubular member is in the vertical position;
   calibrated markings disposed along the length of said tubular member for indicating the degree of resiliency of the game ball in accordance with the rebound of the same from said striking surface, said calibrated markings comprising markings to indicate a dead ball, old ball and live ball, respectively; and
   each of said guides projecting inwardly of said tubular member along the longitudinal length thereof for guiding the game ball to be tested from said opening toward said striking surface and for guiding the game ball during the rebound from said striking surface.

2. A device for testing a game ball as set forth in claim 1 wherein said striking surface is located on one face of an insert fixedly secured within said tubular member.

3. A device for testing a game ball as set forth in claim 2 wherein said striking surface is substantially planar.

4. A device for testing a game ball as set forth in claim 2 wherein said insert is cylindrical.

5. A device for testing a game ball as set forth in claim 2 wherein said insert is made of steel.

6. A device for testing a game ball as set forth in claim 2 wherein said insert has an annular groove therein, said annular groove locking said insert to the tubular member.

7. A device for testing a golf ball as set forth in claim 1 wherein said calibrated markings are located on all three of said guides.

8. A device for testing a golf ball as set forth in claim 7 wherein said calibrated marking to indicate dead ball is nearest to said striking surface and said marking to indicate live ball is nearest to said top opening.

9. A device for testing a golf ball as set forth in claim 7 wherein said calibrated marking to indicate an old ball is located between indications for a dead and live ball.

10. A device for testing a golf ball as set forth in claim 7 wherein said calibrated markings are located on each of said guides, said markings on one guide corresponding with an 80 compressions type golf ball while the markings on the other guides correspond respectively with 90 and 100 compressions-type golf balls.

11. A device for testing a game ball as set forth in claim 10 wherein said tubular member is of a plastics material.

12. A device for testing a game ball as set forth in claim 11 wherein said tubular member is a one-piece molding of plastics material.

13. A device for testing a game ball as set forth in claim 12 wherein said tubular member is molded about a metal insert.

* * * * *